(12) United States Patent
Hosemann

(10) Patent No.: US 12,730,236 B2
(45) Date of Patent: Sep. 8, 2026

(54) DETECTOR MODULE FOR AN X-RAY DETECTOR HAVING A HEATING LAYER

(71) Applicant: Siemens Healthineers AG, Forchheim (DE)

(72) Inventor: Michael Hosemann, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 460 days.

(21) Appl. No.: 18/341,999

(22) Filed: Jun. 27, 2023

(65) Prior Publication Data

US 2024/0004091 A1 Jan. 4, 2024

(30) Foreign Application Priority Data

Jun. 30, 2022 (EP) .................................... 22182306

(51) Int. Cl.
*G01T 1/24* (2006.01)
*A61B 6/03* (2006.01)
*A61B 6/42* (2024.01)

(52) U.S. Cl.
CPC .............. *G01T 1/242* (2013.01); *A61B 6/032* (2013.01); *A61B 6/4208* (2013.01); *G01T 1/244* (2013.01)

(58) Field of Classification Search
CPC ......... G01T 1/242; G01T 1/244; G01T 1/243; A61B 6/032; A61B 6/4208; A61B 6/4241; A61B 6/4266
See application file for complete search history.

(56) References Cited

U.S. PATENT DOCUMENTS

| | | | | |
|---|---|---|---|---|
| 9,547,091 | B2 * | 1/2017 | Ergler | G01T 1/243 |
| 10,866,328 | B2 | 12/2020 | Ergler et al. | |
| 2016/0018536 | A1 | 1/2016 | Ergler et al. | |
| 2018/0120447 | A1 * | 5/2018 | Ergler | G01T 1/244 |
| 2019/0383954 | A1 | 12/2019 | Onouchi | |
| 2020/0158890 | A1 * | 5/2020 | Ergler | G01T 1/2002 |

* cited by examiner

*Primary Examiner* — Uzma Alam
*Assistant Examiner* — Gisselle M Gutierrez
(74) *Attorney, Agent, or Firm* — Harness, Dickey & Pierce, P.L.C.

(57) ABSTRACT

A detector module for an X-ray detector comprises: a stacked structure having a sensor layer, a readout layer, a heating layer, and a wiring unit, wherein the wiring unit is positioned after the heating layer in the stacked structure. The heating layer is partitioned into a plurality of heating subregions, each of which includes at least one heating element, and with each of which contact can be made individually for supplying power. Through the wiring unit, contact is made to each of the plurality of heating subregions of the heating layer, and at least one subset of the plurality of heating subregions is interconnected for the supply of power.

20 Claims, 6 Drawing Sheets

DETECTOR MODULE FOR AN X-RAY DETECTOR HAVING A HEATING LAYER

CROSS-REFERENCE TO RELATED APPLICATION(S)

The present application claims priority under 35 U.S.C. § 119 to European Patent Application No. 22182306.5, filed Jun. 30, 2022, the entire contents of which are incorporated herein by reference.

FIELD

One or more example embodiments of the present invention relate to a detector module for an X-ray detector having a heating layer. One or more example embodiments of the present invention also relate to an X-ray detector comprising a plurality of detector modules, and to a computed tomography device comprising such an X-ray detector.

BACKGROUND

An X-ray detector is employed in imaging applications. For instance, such an X-ray detector is used for computed tomography acquisitions in medical imaging in order to produce a spatial image of an examination region of a patient.

X-ray detectors can be embodied as counting, direct converting X-ray detectors or as integrating, indirect converting X-ray detectors. An X-ray detector, the sensor layer of which is embodied as a direct converting semiconductor layer, allows quantitative and energy-selective sensing of individual X-ray quanta. For example, semiconductor materials in the form of CdTe, CdZnTe, CdTeSe, CdZnTeSe, CdMnTe, GaAs, Si or Ge, which have a high absorption cross-section for X-ray radiation, are suitable for detecting the X-ray quanta. When there is incident X-ray radiation, electron-hole pairs, i.e. pairs of negative and positive charge carriers, are produced in the sensor layer. A voltage applied to the sensor layer or to the surface of the sensor layer separates the charge carriers, which move to the respective oppositely charged electrodes or faces of the sensor layer. The resulting current or a corresponding charge displacement can be evaluated by a sensor electronic circuit connected downstream, which is also referred to below as an evaluation unit or evaluation layer. The sensor layer or sensor unit of a direct converting X-ray detector is usually in a stacked structure with its associated evaluation unit. A stacked structure of this type composed of sensor layer and evaluation unit can also be called a sensor board below.

In particular, direct converting (photon-counting) X-ray detectors must be kept at a constant temperature as precisely as possible during operation. Otherwise image artifacts can arise. In direct converting X-ray detectors, or in the detector modules of a corresponding design, the electrical resistance of the sensor material varies with the X-ray flux. This leads to a change in power loss. This means, however, that a change in the X-ray flux causes a temperature change in the sensor layer, which in turn affects the energy resolution and the counting rate of the X-ray detector. In addition to a time-related temperature change in the sensor layer, the drift behavior of an X-ray detector is also affected by locally different temperatures of the sensor layer. Such temperature gradients arise in particular as a result of uneven heat dissipation from the sensor layer. In addition, an unwanted temperature gradient on the sensor board, or in the sensor layer of the corresponding sensor board, can also occur depending on the operating point of the sensor board. Depending on the setting selected for each of the operating parameters, for instance the mean operating temperature of the detector module or of the sensor material, or the applied supply voltage, there may be a higher current through the sensor material, which even without incident X-ray radiation can lead to a high power loss and hence likewise to a temperature gradient in the sensor layer.

In order to avoid temperature gradients in the sensor layer, thermal coupling to a heat sink over as much of the surface as possible is desirable. However, coupling over the entire surface, and hence uniform heat dissipation, is made more difficult, for example, by parts located on the underside of the sensor board, for instance parts used for connecting to a module electronics circuit, such as passive structural elements or male connectors for data transfer, and/or by other mechanical recesses. Consequently, the heat dissipation through a heat sink is heavily dependent on the design of the sensor board and the geometry of the module structure. In order to stabilize the temperature of the X-ray detector, it is also possible to use heating elements in the sensor board, which can introduce additional heating power. In this case, however, the arrangement and design of the heating elements must be matched to a prevailing, possibly uneven, temperature distribution in the sensor board.

In addition, it is desirable for the development of an X-ray detector for individual components to be developed as independently of each other as possible, or not to be specified or constrained too early in the design process. It is also advantageous if components can be deployed flexibly, for example across different detector geometries. However, the use of costly parts or manufacturing steps for this must always be limited to a sensible level, which under some circumstances may conflict with the aforementioned objectives.

SUMMARY

An object of one or more example embodiments of the present invention is to define a detector module that advantageously can be temperature-stabilized and advantageously takes account of at least some of the aforementioned disadvantages and objectives. A further object of one or more example embodiments of the present invention is to define an X-ray detector and a computed tomography device having a plurality of corresponding detector modules.

At least this object may be achieved by at least the features of the independent claims. The dependent claims and the description below present further advantageous embodiments and developments of the present invention, some of which are inventive in their own right.

An embodiment of the present invention relates to a detector module for an X-ray detector comprising in a stacked structure a sensor layer, a readout layer, a heating layer, and a wiring unit positioned after the heating layer in the stacked structure, wherein the heating layer is partitioned into a plurality of heating subregions, each of which comprises at least one heating element, and with each of which contact can be made individually for supplying power, and wherein via the after-arranged wiring unit, contact is made to each of the heating subregions of the heating layer, and at least one subset of the heating subregions is interconnected for the supply of power.

The X-ray detector module according to an embodiment of the present invention has a stacked structure. The stacking direction can be oriented in particular substantially parallel to the operational direction of incidence of the X-ray radiation. The sensor layer is preferably located in the stacked structure such that it is closest to the X-ray radiation source so that the X-ray radiation is incident in particular directly on the converter unit.

The sensor layer expediently comprises a direct converting semiconductor material, in particular cadmium telluride (CdTe) or cadmium zinc telluride (CdZnTe). Such semiconductor materials allow the direct conversion of the incident X-ray radiation into an electrical signal, and are commercially available in good quality in terms of charge transport properties and homogeneity. The sensor layer can also comprise another semiconductor material in the form of CdTeSe, CdZnTeSe, CdMnTe, GaAs, Si or Ge. Even though temperature stabilization is of particular importance in direct converting detectors, a detector-module design according to an embodiment of the present invention can also comprise a sensor layer having an indirect converting material in combination with a photodiode array. Scintillators, for instance GOS ($Gd_2O_2S$), CsJ, YGO or LuTAG, are often used here as the converter material.

The sensor layer of a detector module can be embodied as a single piece. However, it can also be formed from a plurality of sensor elements placed side by side that together span the sensor layer.

The readout layer can comprise in particular a multiplicity of pixel electronic circuits, wherein each pixel electronic circuit can be designed to process, pixel by pixel and hence in a spatially resolved manner, the electrical signals fed to a pixel electronic circuit from the sensor layer into a digital pixel measurement signal. In other words, such a pixel electronic circuit can at least be designed to process further, in particular to digitize, for instance via an A/D converter (analog-to-digital converter), an electrical signal received from the sensor layer. Moreover, the pixel electronic circuits can also have further circuit elements, for instance a signal amplifier or a comparator. For this purpose, the readout layer, or respective pixel electronic circuits of the readout layer, can be coupled to the sensor layer via electrically conducting connections. The electrically conducting connections between an evaluation unit and a converter unit can be embodied, for example, as solder connections, for instance what are known as bump bonds, as conductive adhesive connections, or else in another way. To minimize any effects on the signal transfer between sensor layer and readout layer, it is advantageous for the sensor layer and readout layer to be located as close as possible.

The readout layer can be embodied as one or more readout chips in the form of an integrated circuit (IC). Each readout chip then provides pixel electronic circuits for the primary processing of the electrical signals from the sensor layer. In particular, the readout layer can comprise one or more application-specific integrated circuits (ASIC(s)), jointly comprised by the readout layer of the detector module.

The readout layer can comprise a housing, which surrounds one such readout chip or a plurality of readout chips. In addition, it is also possible to pot one or more of such readout chips in the form of unhoused “bare dies” (also known as a “bare chip”) into a part using a potting compound, for example a casting resin.

The heating layer comprised by the stacked structure of the detector module is thermally coupled in the stacked structure to the sensor layer. In a projection plane perpendicular to the stacked structure, it covers the planar extent of the stacked structure at least partially. Covering by the heating layer can be understood in the sense that a plurality of heating elements are provided over the surface associated with the heating layer, which heating elements allow heating power, i.e. heat, to be introduced into the stacked structure via this surface. In preferred embodiments, the heating layer extends over at least the majority of the planar extent of the sensor layer. By virtue of the heating layer covering most of this planar extent, it can advantageously allow heating power to be introduced over the entire covered planar region via the heating layer, and thereby facilitate temperature stabilization. The larger the surface covered, the more advantageously can heating power be introduced. In particularly preferred embodiments, in a projection plane perpendicular to the stacked structure, the heating layer covers substantially the entire planar extent of the sensor layer. The heating layer can be thermally coupled to the sensor layer in particular via the readout layer. In this case it is advantageous if the readout layer, comprising a possible housing or at least a partial coating by a potting compound, extends in the projection plane perpendicular to the stacked structure over at least the majority of the surface of the sensor layer. This can make it possible to introduce heating power into the sensor layer via the readout layer over as large a surface as possible.

The heating layer has heating elements that are designed for introducing heating power into the stacked structure when they are being supplied with power via a power unit during operation. The heating layer hence allows the introduced heating power to contribute to temperature stabilization of the detector module and, for example, to counteract temperature gradients within the stacked structure or the sensor layer. The heating elements can be embodied as simple heating resistances. They can be embodied as conductor loops comprised by the heating layer. These can be embedded in a non-conducting material, in particular a plastics material, or applied to such a material. For example, the non-conducting material can correspond to a printed circuit board material or to the housing material or potting material of the readout layer. The heating elements of the heating layer can be located substantially within a plane.

Each heating subregion of the heating layer covers one subregion of the planar extent of the heating layer. In other words, a heating subregion covers a surface subregion of the total surface of the stacked structure covered by the heating layer. Each heating subregion comprises a heating element which, with the supply of power, is designed to heat the associated surface region of the stacked structure, which surface region is covered by the heating subregion. Contact can be made individually with each heating subregion for supplying power. In other words, each heating subregion has contact points that facilitate the supply of power to the respective heating elements of the heating subregion. For example, the heating layer is partitioned into more than three heating subregions, for instance specifically 9, 16 or 25.

The partitioning into heating subregions provides a spatial resolution, which is primarily possible by virtue of the heating layer, at which resolution a heating power to be introduced into the stacked structure can be spatially adapted by it being possible to drive, or supply with power, the heating subregions differently. The larger the number of heating subregions, the finer the heating power distribution can be adapted by the heating layer and subsequent wiring unit. The partitioning can be uniform, i.e. the heating subregions can each cover a subsurface of the same size, and can be arranged in a regular manner over the surface of the heating layer. In particular, the heating subregions of the heating layer can have the same design, i.e. can be designed to emit the same heating power given identical boundary conditions and the same supply of power. They can comprise in particular identical heating elements. However, they can also cover different surface areas and/or be arranged in an irregular manner. A substantially uniform arrangement or identical design can constitute an advantageously simple implementation, however, because the complexity is minimized in this case.

In the detector module according to an embodiment of the present invention, a wiring unit, via which contact is made with the heating subregions for the supply of power, is positioned after the heating layer. The wiring unit is positioned after the heating layer in the stacked structure in the sense that it is located in the stacked structure after the heating layer along the operational direction of beam incidence. The wiring unit can follow the heating layer directly in the stacked structure. It is also conceivable, however, that a further layer is located between the heating layer and the wiring unit, in which case contact between the heating layer and the wiring layer is then provided via this layer. If the wiring unit follows the heating layer directly in the stacked structure, contact between the contact points of the heating layer and respective mating contact points provided on the wiring unit can be made, for instance, directly via a solder connection. In other embodiments, correspondingly suitable lines for the electrically conducting connection between the heating layer and the wiring layer are provided. In addition, the wiring unit has conductor tracks for feeding the power to the heating subregions. The wiring unit can have substantially the same planar extent as the heating layer. The wiring unit has at least such a planar extent that allows the contact points to make contact with the heating subregions.

Furthermore, in preferred embodiments, the wiring unit is a part of the detector module that is separate from the heating layer, facilitating independent manufacture and adaptation of the wiring unit, which is not placed in contact with the heating layer until the detector module is assembled. In a preferably inexpensive and simple variant, the wiring unit is embodied as a printed circuit board. However, an embodiment in the form of, for example, a carrier ceramic having appropriate conductor tracks, or similar, is also conceivable, for example.

In addition to the wiring of the heating subregions of the heating layer, the wiring unit can also serve as a carrier unit for the stacked arrangement and/or as a substrate for the signal transfer from the readout layer of the detector module to a downstream module electronic circuit, or vice versa. Appropriate lines designed for the signal transfer can be provided for this purpose in the wiring unit.

At least one subset of the heating subregions is interconnected via the wiring unit for the supply of power. An interconnection comprises that the heating subregions of the subset are connected together via suitable lines. This can comprise a parallel connection and/or a series connection of the heating subregions of the subset. There are usually a plurality of subsets, with the heating subregions of a particular subset being interconnected. For operating the detector module, each subset can then be connected via the wiring unit to a shared power unit for the supply of power. Further lines can be provided for operating the heating layer, which lines lead from the wiring unit to one or more power units, each of which is designed to supply power to the heating subregions connected thereto via the wiring unit.

The interconnection of the heating subregions is based on the consideration that there are usually heating subregions in the detector module that, during operation of the detector module, have a similar or identical heating power requirement to other heating subregions of the detector module, or else the respective heating power requirements thereof are in a fixed ratio with respect to each other. The suitable interconnection of these heating subregions via the wiring unit allows power to be supplied to these heating subregions jointly. This contributes to particularly cost-effective deployment of the detector module, because for operating the detector module, a dedicated heating circuit with a dedicated power unit does not need to be provided for each individual heating subregion, which would involve high expenditure for the cabling and would require numerous expensive power units for the supply of power, needing a large amount of space. Furthermore, the implementation of a partitioned heating layer and an after-arranged wiring unit makes it possible to provide in the detector module as generically developed and universally deployable a heating layer as possible, which, by virtue of the provided partitioning thereof, provides the facility to adapt to the conditions that actually exist. Yet this is primarily independent of further components of the detector module, for instance the location of male connectors for data transfer or the configuration of an adjoining heat sink or module carrier, and hence can be developed and implemented in the stacked structure independently of said components. Adaptation to the actually existing heating power requirement of the detector module for the most cost-effective driving and supply of power possible is then achieved by the interconnection of the heating subregions via the wiring unit. By such an implementation, the detector module can be adapted relatively simply and economically, even at a later stage of the design and development phase, to actual, possibly also altered, conditions, by merely having to adapt the wiring unit of the detector module. In addition, simple transferability of the design of the detector module across different types of detector is possible more easily. For example, it is thereby possible to provide, for different detector geometries having differently embodied heat sinks and cabling, a unit composed of sensor layer, readout layer and heating layer, which unit can be deployed as generically as possible and can then be adapted via the wiring unit to the actually existing distribution of the heating requirement. The wiring unit, for instance in the form of a printed circuit board, can be provided and adapted inexpensively and simply.

In advantageous embodiments, the interconnection of the heating subregions via the wiring unit is adapted to the heating power requirement in the stacked structure, in particular the planar distribution of the heating power requirement in a projection plane perpendicular to the stacked structure. This can be measured, for example, during operation of a provisional detector module or else calculated and/or simulated on the basis of known geometries and arrangements, for instance the embodiment of a heat sink intended for the detector module. Based on such considerations and calculations, an interconnection to be provided can be derived and implemented.

The interconnection of the subset of the heating subregions via the wiring unit can comprise a parallel connection and/or series connection of heating subregions. In particular, those heating subregions associated with surface regions of the stacked structure that have the same heating power requirement can be interconnected such that they can be connected to a shared supply of power. In expedient implementations, this can comprise that those heating subregions of the heating layer that are associated with surface regions of the stacked structure that have the same heating power requirement are interconnected in parallel. These can then be connected to a shared power unit for an identical supply of power and drive. A series connection of heating subregions can also be provided, however.

In a further embodiment, the interconnection of the at least one subset of the heating subregions via the wiring unit can comprise a combination of a parallel connection and a series connection of heating subregions of the subset, so that, when power is being supplied, the interconnection sets a fixed ratio between the sub-powers present in the respective heating subregions. Hence even heating subregions associated with surface regions of the stacked structure that have a different heating power requirement can be connected to a shared supply of power, wherein, depending on the specific interconnection, fractions of the total power provided by the power unit may be available as a sub-power in the subregions. Through a suitable combination of parallel connection and series connection of heating subregions via the wiring unit, it is hence possible to establish a relative ratio of the respective heating powers achieved in the interconnected heating subregions, if these are supplied by a shared power unit. This is advantageous when the heating power requirement in the stacked structure can also be accommodated by a ratio established in such a way. Given favorable geometric ratios, the number of power units needed for operating the detector module and the cabling expenditure can thereby be reduced further. In particular, there can be a plurality of subsets of heating subregions, wherein at least one of these subsets can be interconnected using a combination of a parallel connection and a series connection. Other subsets can also be interconnected solely via parallel connections or series connections.

The detector module can comprise in particular a number of power units, wherein each subset of the heating subregions that is interconnected via the wiring unit is connected to a shared power unit for the supply of power. The number of power units is determined by the number of interconnected subsets of heating subregions. The power unit(s) can be located on an electronics unit that is separate from the stacked structure, for example a printed circuit board, with suitable lines leading from the stacked structure to the power units. A separate electronics unit can advantageously offer enough space for locating the power units, whereas the stacked structure itself can be kept as compact as possible, which can make it possible for the stacked structures to be placed side by side for a larger detection surface and, possibly, also optimum heat dissipation therefrom. In addition, it is possible to replace individual components more easily in the event of a fault.

In advantageous embodiments, the power provided by a particular power unit for the heating subregions connected thereto is based on an expected and/or measured temperature in the stacked structure. It is hence advantageously possible to adjust the heating power requirement in the stacked structure and thus the necessary heating power, and to drive the particular power unit accordingly. In particular, a temperature variation during operation or during different operating parameters and/or environmental parameters of the detector module can be taken into account advantageously. This can comprise in particular that a temperature distribution in a projection plane perpendicular to the stacked structure and, if applicable, also the variation thereof over time or the dependency thereof on different operating parameters and/or environmental parameters are measured and/or calculated or estimated, wherein the power provided by a particular power unit is set or regulated on the basis of the temperature distribution. The power provided by each power unit is advantageously adapted to the existing heating power requirement of the heating subregions associated with this particular power unit. An expected temperature or temperature distribution can be based on previously performed measurements during operation of the detector module. An expected temperature or temperature distribution can be based on calculations or simulations. Particularly preferably, the setting or regulation of a provided power by a particular power unit is based on a measured temperature or temperature distribution in the stacked structure. Direct temperature information can advantageously be used to set or regulate the power units. In particular, a particular power unit can have a closed-loop control circuit, and be designed to regulate a provided power on the basis of a temperature in the stacked structure.

According to an embodiment variant, at least one temperature sensor is located for this purpose in the stacked structure. Setting or regulating the power can hence be based advantageously on at least one measured temperature value in the stacked structure, and the currently measured temperature can be taken into account. In advantageous embodiments, a plurality of temperature sensors are located in the stacked structure, so that a current temperature distribution in a projection plane perpendicular to the stacked structure can be sensed in an improved, spatially resolved manner from measured values. The drive and/or regulation of the power provided in the heating subregions can be implemented on the basis thereof. It is also possible, however, for example, to derive an expected temperature distribution in a projection plane perpendicular to the stacked structure on the basis of an individual measured temperature value. Such an implementation can comprise that the expected temperature distribution in the stacked structure during operation of the detector module was measured in advance in measurements and/or simulations in conjunction with a measured temperature value. The drive and/or regulation of the heating power in the heating subregions can then be implemented on the basis of the measured temperature value and the expected temperature distribution derived therefrom. In an advantageous, expedient embodiment variant, the at least one temperature sensor is integrated in the readout layer.

In advantageous configurations of the detector module, the heating layer is applied to a face of the readout layer or integrated in the readout layer. It is advantageous to locate the heating layer as close as possible to the sensor layer, because the temperature of the sensor is the parameter crucial to image quality. Applying to a face of the readout layer or integrating in the readout layer furthermore constitutes an embodiment variant that is easy to provide, because in this case, required heating elements and lines are easy to integrate and apply. For example, the heating elements of the heating layer can be embedded in a housing or a coating of the readout circuits of the readout layer, or applied on a face of a housing or coating of the readout circuits. The heating elements of the heating layer can be in the form of heating resistances or heating loops applied on a face of the readout layer or integrated in the readout layer. For a subsequent wiring unit to be able to make contact easily with the heating elements of the heating layer, it can be particularly expedient to provide the heating layer at, or on, a side of the readout layer that faces away from the sensor layer. This can be advantageous for the minimum possible interference in transferring the signals from the sensor layer to the evaluation layer.

In addition, the stacked structure of the detector module according to an embodiment of the present invention can be located on a module carrier, which is thermally coupled to the sensor layer via the stacked structure. The module carrier can be designed to fix a detector module mechanically in a housing comprising the detector module. A suitable fixing mechanism, device, or alternatively, means, and alignment mechanism, device, or alternatively, means, can be provided for this purpose on the module carrier. The module carrier is preferably embodied as a metallic heat sink which, for the purpose of stabilizing the temperature of the detector module, allows heat to be removed from the stacked structure and in particular from the sensor layer. The wiring of the heating layer is than adapted in particular to the configuration of the module carrier and hence to regions in which the degree of heat removal differs, achieving equalization of the temperature distribution in the stacked structure.

The wiring unit in the stacked structure is expediently connected to a module electronic circuit via the module carrier. The module electronic circuit can be used for readout, collection and/or further processing of the measurement data from the readout layer. For this purpose, the module electronic circuit can have further active or passive structural elements that are designed to provide the necessary functionalities. Furthermore, the module electronic circuit can be used for the transfer of drive data and for the supply of power for operating the stacked structure.

In particular, the module electronic circuit can comprise the number of power units for supplying the heating layer with power. The module electronic circuit usually offers enough space for locating the power units. The power units are still advantageously provided relatively close to a particular stacked structure. It is likewise possible to replace individual components more easily in the event of a fault.

Furthermore, according to an embodiment, the detector module can comprise a number of stacked structures located adjacent to one another on the module carrier. For example, the detector module can comprise 2, 3 or 4 identically embodied stacked structures. A greater extent of the total detection surface of the module can be achieved advantageously by the side-by-side placement. The plurality of stacked structures can be assigned to a shared module electronic circuit, and supplied or driven via said circuit. The supply of power to the heating layer of each stacked structure can preferably be controlled or regulated independently of the others. It is thereby possible to take into account, if applicable, different boundary conditions of the stacked structures, for instance a supply of air from one side in the cooling of the detector module. In this case, cooling air used for the cooling flows along the detector module and is heated. Accordingly, the sensor layer of a detector-module sensor board located at the start of the cooling-air path is cooled more strongly than the sensor layer of a sensor board located at the end of the cooling path.

Embodiments of the present invention also relate to an X-ray detector for acquiring images of an X-rayed object, comprising a plurality of adjacently located detector modules according to one of the previously described variants. The number of detector modules deployed in an X-ray detector and hence the number of sensor boards, depends on their size and on the total sensor surface area required. The X-ray detector can comprise further elements, for example carrier constructions for mounting the detector modules, cooling-air intakes and outlets for improved heat removal from the detector modules, or an anti-scatter grid, which, in the direction of incidence of the beam, is located in front of the sensor layer of the detector modules.

All the embodiment variants described above in connection with the detector module according to the present invention can also be implemented correspondingly in the X-ray detector. The description relating to the detector module and the aforementioned advantages of the detector module can also be applied accordingly to the X-ray detector according to the present invention.

In particular, embodiments of the present invention further relate to a computed tomography device comprising an X-ray detector as previously described. The computed tomography device comprises opposite thereto an X-ray source, which is designed to shine X-ray radiation onto the X-ray detector. Said X-ray source and X-ray detector are located on a rotor that allows rotation about a rotational axis. The computed tomography device can also comprise more than one X-ray detector.

For acquiring a computed tomography image dataset, an object to be imaged is usually positioned between the X-ray source and the detector unit along the rotational axis, through which object the X-ray source beams radiation.

In the context of the present invention, features described with regard to different embodiments of the present invention can also be combined to give further embodiments of the present invention. In addition to the embodiments of the present invention described explicitly in this application, a person skilled in the art will be able to arrive at various further conceivable embodiments of the present invention without departing from the scope of the present invention defined by the claims.

The use of the indefinite article "a" or "an" does not rule out the possibility of there also being more than one of the feature concerned. The use of the expression "has" does not exclude the possibility of the terms linked by the expression "has" being identical. For example, the computed tomography device has the computed tomography device. The use of the expression "unit" does not exclude the possibility that the subject to which the expression "unit" relates has a plurality of components that are spatially separate from one another.

BRIEF DESCRIPTION OF THE DRAWINGS

The present invention is described below using exemplary embodiments with reference to the accompanying figures. Schematic, highly simplified diagrams that are not necessarily to scale appear in the figures, in which:

FIG. 6 shows a schematic illustration of the interconnection of the plurality of heating subregions of an exemplary detector module according to a first variant;

FIG. 7 shows a schematic illustration of the interconnection of the plurality of heating subregions of an exemplary detector module according to a second variant.

DETAILED DESCRIPTION

Figures 1, 2:
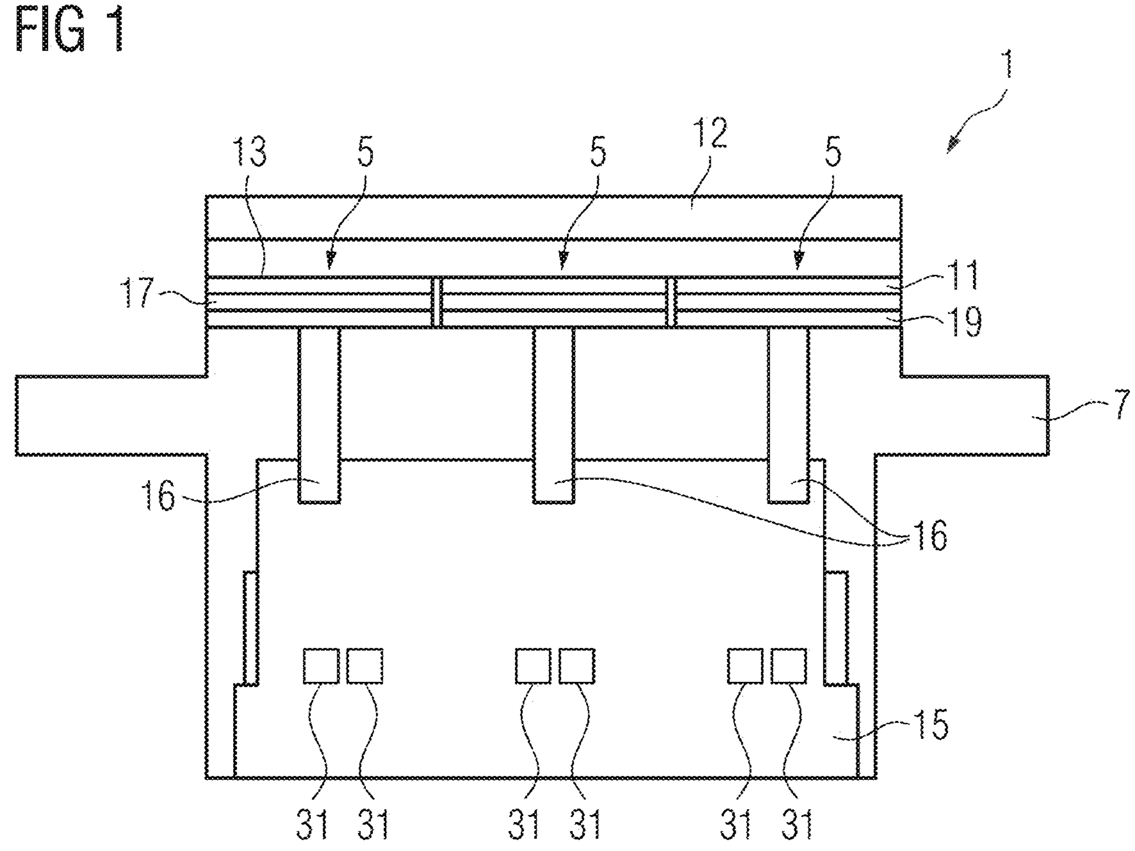
FIG. 1 shows an exemplary embodiment of a detector module for an X-ray detector having a plurality of stacked structures located next to one another.
FIG. 2 shows a stacked structure of an exemplary detector module.

FIG. 1 shows an exemplary embodiment variant of a detector module 1 for an X-ray detector. The embodiment shown comprises a plurality of identically embodied stacked structures 5 located next to one another. A detector module according to an embodiment of the present invention can also be embodied differently, however. For example, a detector module 1 according to an embodiment of the present invention can also comprise just one stacked structure 5. A stacked structure 5 comprising a sensor layer 11, an evaluation layer 17, a heating layer 2 (not shown explicitly here for the sake of clarity) and a wiring unit 19, which stacked structure can be used in a detector module 1 according to an embodiment of the present invention, is explained below in greater detail with reference to FIG. 2.

In the case of the detector module 1 shown by way of example in FIG. 1, the stacked structures 5 are located on a metallic module carrier 7. In addition, these are connected via the module carrier 7 to a module electronic circuit 15, from which outgoing data lines 16 run to the respective stacked structures 5, called sensor boards. The module electronic circuit 15 can be used for readout, collection and/or further processing of the measurement data from the readout layer 19. Furthermore, the module electronic circuit 15 can be used for the transfer of drive data and for the supply of power for operating the stacked structure 5. In particular, a number of power units 31 for supplying power to the heating layer 2 according to an embodiment of the present invention of each stacked structure 5 can be comprised by the module electronic circuit 15 or located thereon. The module electronic circuit 15 usually offers enough space for locating the power units 31. In addition, the sensor face 13 of each stacked structure is overlaid by a collimator 12, which is used to produce a parallel beam path and to avoid scattered radiation.

The module carrier 7 also serves here as a heat sink for dissipating heat from the stacked structures 5. The module carrier 7 is thermally coupled via the stacked structure 5 to the sensor layer 11 of a given stacked structure 5.

FIG. 2 illustrates more precisely an embodiment variant of a stacked structure 5 of a detector module 1 according to an embodiment of the present invention, which stacked structure can also be comprised by a module as in FIG. 1. The stacked structure 5 comprises the sensor layer 11 having the sensor face 13. The sensor layer 11 is used to detect X-ray radiation. For this purpose, in the installed state inside an X-ray detector, a high voltage is applied to the sensor face 13 via an electrode (not shown). The sensor layer comprises in preferred embodiments a direct converting semiconductor material, in particular cadmium telluride (CdTe) or cadmium zinc telluride (CdZnTe).

In addition, the stacked structure 5 comprises a readout layer 17. In the detector module 1 shown, the sensor layer 11 is applied on the readout layer 17. Between the readout layer 17 and the sensor layer 11 are provided electrically conducting connections (not shown here), for instance solder connections in the form of "bump bonds", which allow signal transfer between the sensor layer 11 and the readout layer 17.

The readout layer 17 can comprise, for example, one or more application-specific integrated circuits (ASIC(s)) surrounded by a housing. In alternative variants, it is also possible to pot one or more of such readout chips in the form of unhoused "bare dies" (also known as a "bare chip") into a part using a potting compound, for example a casting resin.

In addition, the stacked structure 5 comprises a heating layer 2, and a wiring unit 19 positioned after the heating layer 2 in the stacked structure. In the example shown, the heating layer 2 is applied to a face of the readout layer 17. The heating layer 2 can be applied on a housing or a coating of the readout layer 17 by a potting compound. In alternative variants, however, the heating layer can also be integrated in the readout layer 17, for instance in a housing. The heating layer 2 has heating elements 27 in the form of heating resistances or conducting loops that are designed to introduce heating power into the stacked structure 5 when they are supplied with power during operation via a power unit 31. For example, the heating resistances may be applied directly onto the housing or coating of the readout layer 17, or alternatively embedded therein in the form of a layer.

In the exemplary embodiment shown, the heating layer 2 is thermally coupled in the stacked structure 5 to the sensor layer 11 via the readout layer 17. According to an advantageous embodiment, it covers in a projection plane perpendicular to the stacked structure 5 the planar extent of the stacked structure 5 and hence also the entire surface of the sensor layer 11. It is advantageous for the heating layer 2 to extend over at least the majority of the planar extent of the sensor layer 11 because this allows heating power to be introduced over the entire covered planar region via the heating layer 2, and thereby facilitates temperature stabilization. There may also be embodiments, however, in which coverage over the entire surface is not achieved.

Figure 3:
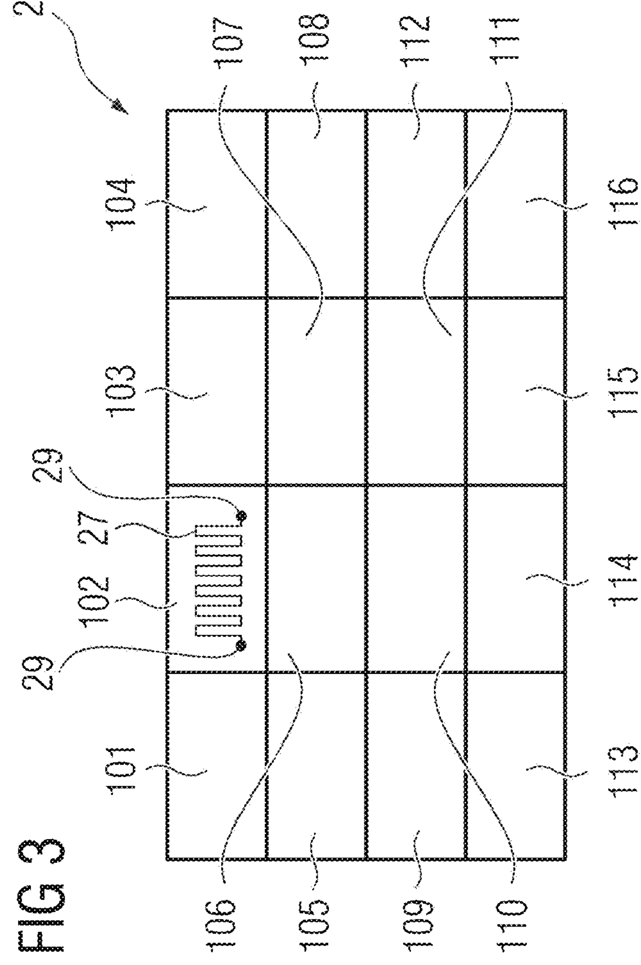
FIG. 3 shows a schematic illustration of a heating layer having a plurality of heating subregions of an exemplary detector module.

As indicated in FIG. 3 by way of example, the heating layer 2 is partitioned into a plurality of heating subregions 101,102, . . . 116, each of which comprises at least one heating element 27 (depicted here only in heating subregion 102) and with each of which contact can be made individually for supplying power. For this purpose, each heating element 27 of a heating subregion 101,102, . . . 116 has contacts 29, via which the respective heating elements 27 of the heating subregions 101,102, . . . 116 can be supplied with power.

Each heating subregion 101,102, . . . 116 of the heating layer 2 covers one subregion of the planar extent of the heating layer 2 in FIG. 2. In other words, a heating subregion covers a surface subregion of the total surface of the stacked structure 5 covered by the heating layer 2, and is designed to heat this surface subregion when the heating element 27 is supplied with power. In the illustration shown, the heating subregions 101,102, . . . 116 have a uniform and identical design. There may also be other embodiments, however. For example, respective heating subregions can cover surfaces that differ in size. In particular, also the heating elements 27 may differ from one another.

The wiring unit 19 is used to make contact with each of the heating subregions 101,102, . . . 116 of the heating layer 2 for the supply of power, and to interconnect at least one subset of the heating subregions 101,102, . . . 116 for the supply of power. An interconnection comprises that the heating subregions of the subset are connected together via suitable lines. For operating the detector module 1, each subset can then be connected via the wiring unit 19 to a shared power unit 31 for the supply of power. For this purpose, the wiring unit 19 has conductor tracks for feeding the power to the heating subregions 101,102, . . . 116.

The interconnection can comprise a parallel connection or a series connection of the heating subregions of the subset. In particular, those heating subregions associated with surface regions of the stacked structure 5 that have the same heating power requirement can be interconnected such that they can be connected to a shared power unit 31 and supplied jointly with power. An interconnection of the at least one subset of the heating subregions via the wiring unit 19 can also comprise a combination of a parallel connection and a series connection of heating subregions of the subset, so that, when power is being supplied, the interconnection sets a fixed ratio between the sub-powers present in the respective heating subregions. There are usually a plurality of subsets, wherein the heating subregions of a particular subset can be interconnected and supplied jointly with power.

The wiring unit 19 in the exemplary stacked structure 5 in FIG. 2 follows the heating layer 2 directly, so that contact between the contact points 29 of the heating layer and respective mating contact points provided on the wiring unit 19 can be made advantageously easily directly, for instance via a solder connection. Other embodiments are also conceivable, however.

In addition to the wiring of the heating subregions 101, 102, . . . 116 of the heating layer 2, the wiring unit 19 can also serve as a carrier unit for the stacked arrangement and/or as a substrate for the signal transfer from the readout layer 17 of the detector module to a downstream module electronic circuit, or vice versa. Appropriate lines designed for the signal transfer can be provided for this purpose in the wiring unit 19.

Furthermore, the wiring unit 18 can be connected to subsequent components via a male connector 18 and lines 16. For instance, lines can be provided thereby for operating the heating layer 2, which lead from the wiring unit 19 to one or possibly more power units 31 designed to supply power to heating subregions 101,102, . . . 116 connected thereto via the wiring unit 19.

Figure 4:
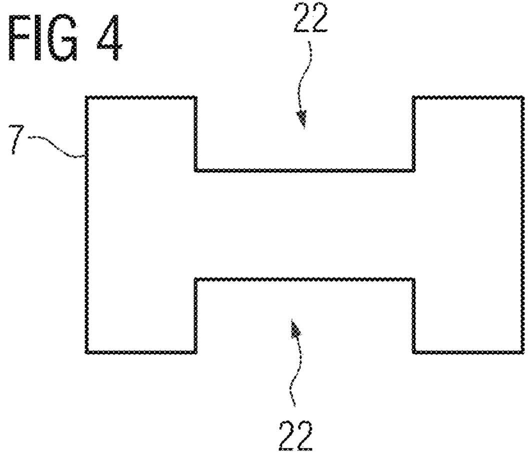
FIG. 4 shows a plan view of an exemplary module carrier.
Figure 5:
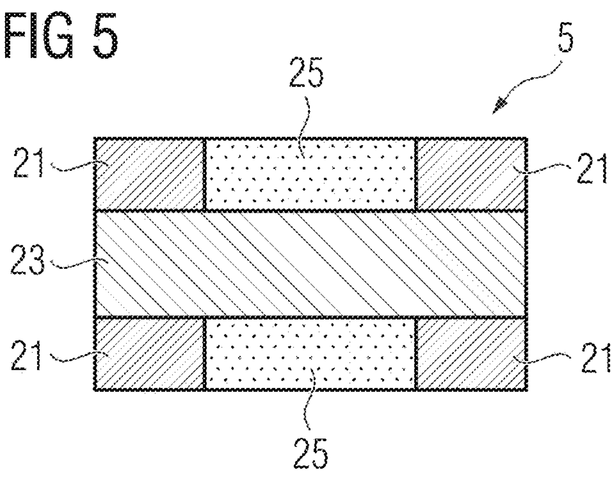
FIG. 5 shows a schematic illustration of a spatial distribution of the heating power requirement in a stacked structure.

FIGS. 4 and 5 are intended to illustrate a possible dependency of the heating power requirement in the stacked structure 5 of a detector module 1 on a mechanical design of a module carrier 7 for the detector module 1. FIG. 4 shows a plan view of the geometrical configuration of a module carrier 7, such as can be provided for a single stacked structure 5. The module carrier in this embodiment has recesses 22 for a plug-in connection 18 to the stacked structure 5 and/or for data lines 16 from the stacked structures 5 to a downstream module electronic circuit 15. Consequently, the stacked structure 5 does not lie over the entire surface of the module carrier 7, resulting in uneven heat dissipation from the stacked structure through the module carrier 7.

FIG. 5 shows a possible resultant spatial distribution of the heating power requirement in the projection plane perpendicular to the stacked structure 5 when said stacked structure is positioned on such a module carrier 7. Only low heat removal takes place in the regions 25 corresponding to the regions of the recesses 22. The heat requirement is thereby low. A large amount of heat is removed via the center bridge of the module carrier; the heating requirement in the region 23 is consequently high.

At the side struts, i.e. the regions 21, the heating requirement can lie between the two extremes, for example.

A generic heating layer 2 according to an embodiment of the present invention, for instance as illustrated schematically in FIG. 2, can be matched, via a suitable interconnection by the wiring unit 19, advantageously to said expected distribution of the heating power requirement in order to ensure cost-efficient provision and operation of the detector module 1. In the same way, a stacked structure 5 having a generic heating layer 2 could also be adapted relatively easily, to be precise merely by adapting the wiring unit 19, to other mechanical designs of the module carrier 7, while still being able to ensure that the heating layer 2 is located advantageously as close as possible to the sensor layer 11.

Figure 6:
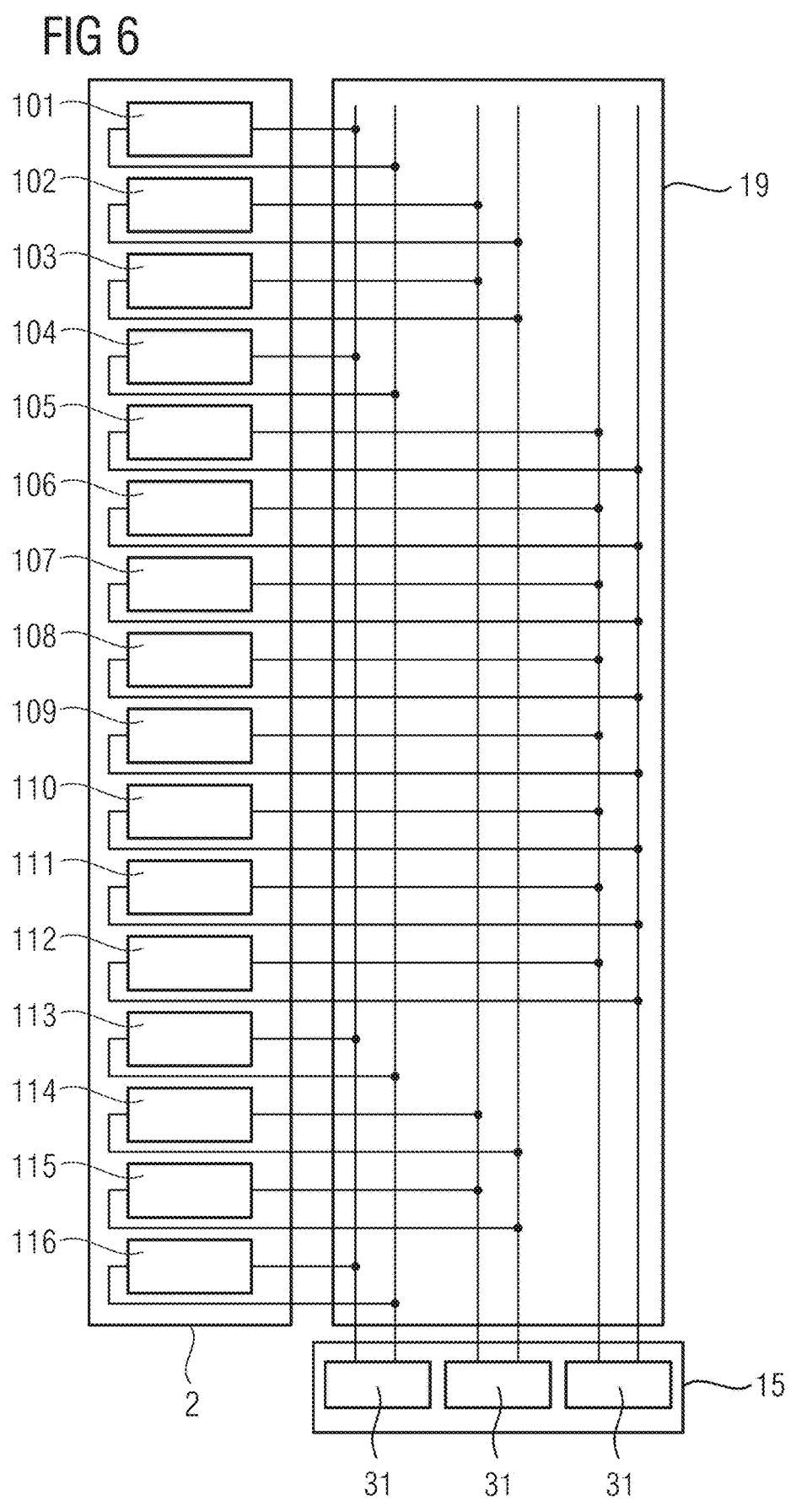
Figure 7:
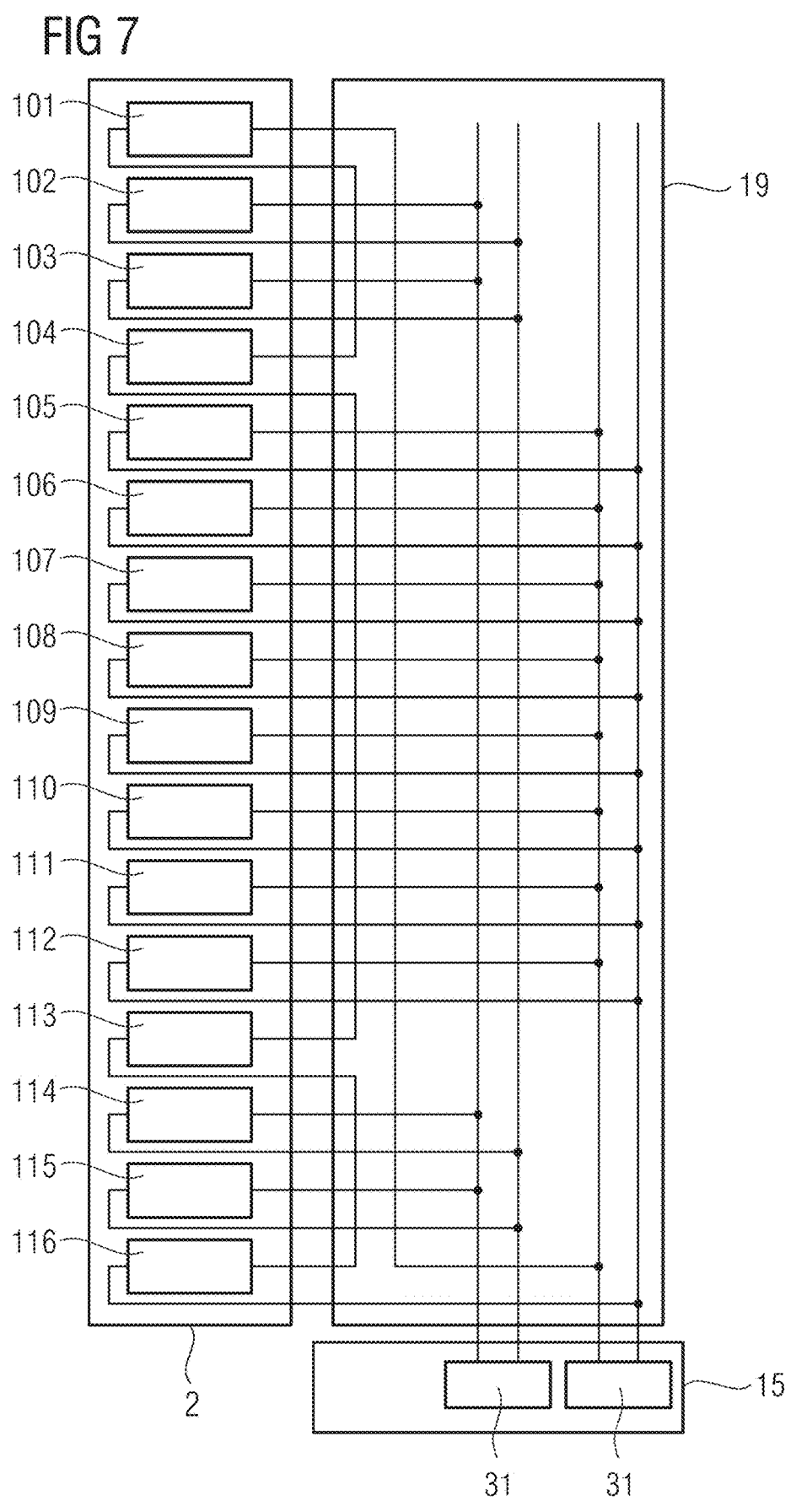

FIGS. 6 and 7 show examples of interconnections of the heating subregions 101,102, . . . 116 of a heating layer 2 of a detector module 1 via the wiring unit 19 when this is partitioned as depicted in FIG. 2. The shown examples of wirings of the heating subregions 101,102, . . . 116 take account of an assumed distribution of the heating power requirement in the stacked structure 5 as illustrated with reference to FIG. 5. This is purely by way of example, however. In other embodiment variants, it is also possible to implement other wirings matched to the conditions that exist in each case.

FIG. 6 shows a plurality of subsets of heating subregions that are each connected via the wiring unit in a parallel connection to a power unit 31 on a module electronic circuit. The first subset comprises the heating subregions 101, 104, 113 and 116. The second subset comprises the heating subregions 102, 103, 114 and 115. The third subset comprises the heating subregions 105 to 112. The heating subregions that are connected jointly to a power unit 31 are each supplied with the same power. By virtue of such an interconnection, each of the heating subregions can all be supplied with power according to their heating power requirement, while cost-efficiently only a smaller number of power units 31 are needed.

Given favorable geometric ratios, the number of power units 31 needed can be further reduced by a suitable combination of series and parallel connections of heating subregions 101,102, . . . 116. An interconnection of the at least one subset of the heating subregions 101,102, . . . 116 via the wiring unit comprising a combination of a parallel connection and a series connection can be used to set a fixed ratio between the sub-powers present in the respective heating subregions when power is being supplied by a shared power unit 31. FIG. 7 shows an example of this in which the heating subregions 101, 104, 113 and 116 and the heating subregions 105 to 112 are connected to a shared power unit 31 via a combination of a series and parallel connection. In this case, in each of the heating subregions 101, 104, 113 and 116 is achieved 1/16 of the power of the other heating subregions 105 to 112 on the same power unit 31. Of course the option of such an interconnection is dependent on the expected distribution and the variation over time of the heating power requirement in the sense that the fraction of supplied power is thereby established in the wiring and hence this does not allow any independent, for example time-variable, adaptation within the subset of the heating subregions interconnected in such a way.

In advantageous embodiments of a detector module 1 according to an embodiment of the present invention, as described previously with reference to the figures, the power provided by a particular power unit 31 for the heating subregions connected thereto is based on an expected and/or measured temperature in the stacked structure 5. In particular, a temperature variation during operation or the temperature under different operating parameters and/or environmental parameters of the detector module 1 can be taken into account advantageously. This can comprise in particular that a temperature distribution in a projection plane perpendicular to the stacked structure 5 and, if applicable, also the variation thereof over time or the dependency thereof on different operation parameters and/or environmental parameters are measured and/or calculated or estimated, wherein the power provided by a particular power unit is set or regulated on the basis of the temperature distribution. The power provided by each power unit 31 can advantageously be adapted to the existing heating power requirement of the heating subregions associated with this particular power unit 31. In this case, for measuring the temperature, in particular at least one temperature sensor 30 can be located in the stacked structure, as FIG. 2 also indicates. In advantageous embodiments, a plurality of temperature sensors 30 are located in the stacked structure, so that a current temperature distribution in a projection plane perpendicular to the stacked structure can be sensed in an improved, spatially resolved manner from measured values. A drive and/or regulation of the power provided in the heating subregions can be implemented on the basis thereof. In an advantageous, expedient embodiment variant, the at least one temperature sensor 30 is integrated in the readout layer.

Figure 8:
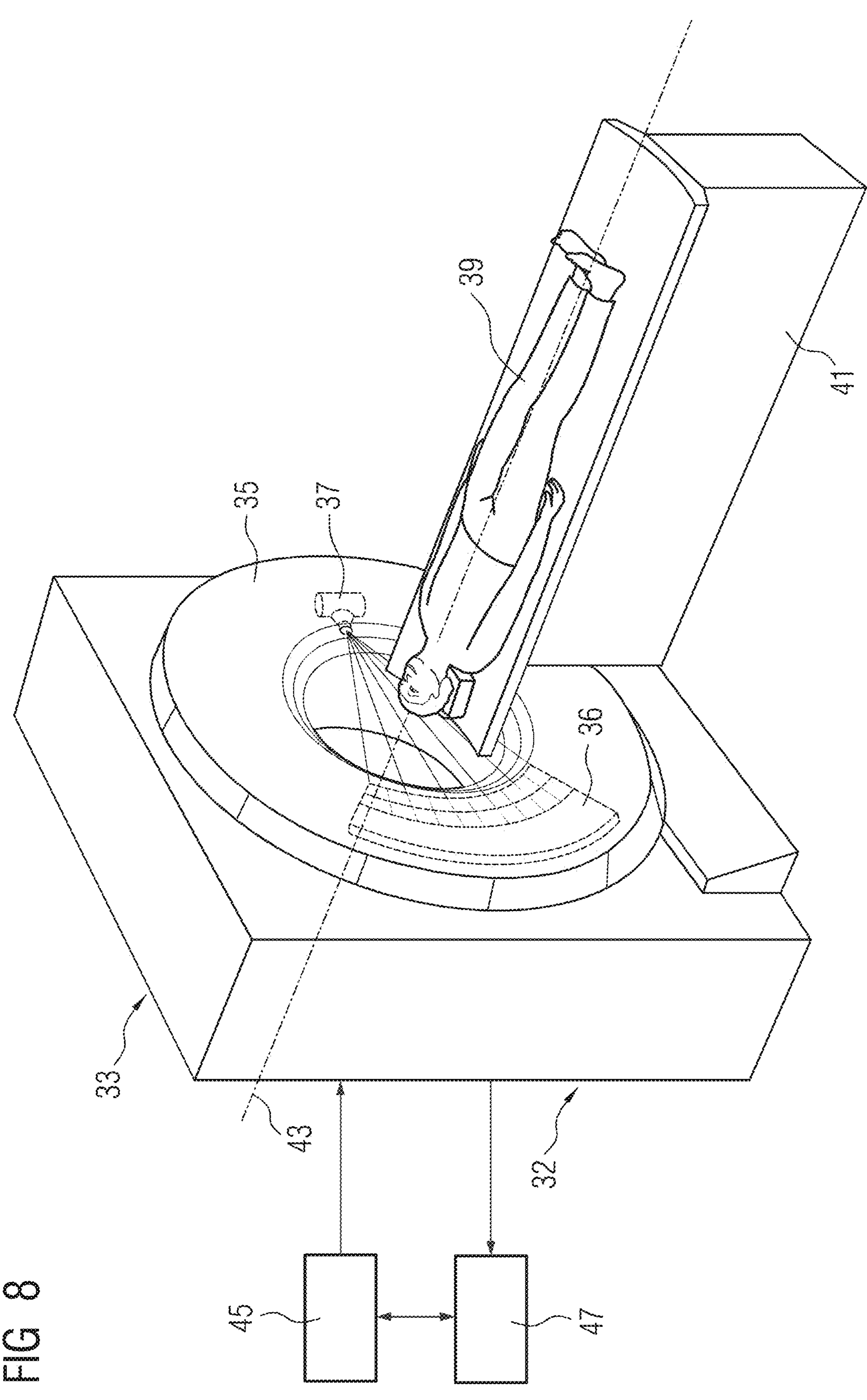
FIG. 8 shows a computed tomography device.

FIG. 8 shows an exemplary embodiment of a computed tomography device 32 having an X-ray detector 36, which comprises at least one detector module 1 according to an embodiment of the present invention, and an X-ray source 37 opposite thereto. The X-ray source 37 is designed to shine X-ray radiation onto the X-ray detector 36. The X-ray source 37 and the X-ray detector are comprised by a gantry 33 and located on a rotor 35. The rotor 35 can rotate about the rotational axis 43. The object under examination 39, in this case a patient, is supported on the patient couch 41 and can be moved along the rotational axis 43 by the gantry 33. A computing unit 45 is used to control the computed tomography device 32 and/or to compute sectional images or volumetric images of the object. A reconstruction apparatus 45 in the form of a computer system is designed to reconstruct X-ray image data on the basis of the data from the X-ray detector 36 of the computed tomography device. A further computer system serves as an operator console 47. The software installed on the operator console 47 allows the operator to control the operation of the computed tomography device, for instance selecting a protocol, starting the scanner, etc. The reconstruction apparatus 45 and the operating console 47 can also be embodied as a computer system.

The X-ray detector 36 of said medical imaging device 32 can comprise in particular a detector module 1 or even a plurality of detector modules 1. In particular, the detector modules 100 are then usually located next to one another, at least in the direction of rotation, so that by placing the respective detection surfaces of the detector modules 100 side by side an advantageously large total detection surface can be formed overall.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as “processing” or “computing” or “calculating” or “determining” of “displaying” or the like, refer to the action and processes of a computer system, or similar electronic computing device/hardware, that manipulates and transforms data represented as physical, electronic quantities within the computer system’s registers and memories into other data similarly represented as physical quantities within the computer system memories or registers or other such information storage, transmission or display devices.

In this application, including the definitions below, the term ‘module’ or the term ‘controller’ may be replaced with the term ‘circuit.’ The term ‘module’ may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects.

Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A detector module for an X-ray detector, the detector module comprising:

a stacked structure including a sensor layer, a readout layer, a heating layer, and a wiring unit, the wiring unit being positioned after the heating layer in the stacked structure, wherein the heating layer is partitioned into a plurality of heating subregions, each of which includes at least one heating element, and each of which is configured to be individually supplied with power, the wiring unit contacts each of the plurality of heating subregions of the heating layer, and at least one subset of the plurality of heating subregions is interconnected for supply of power.

2. The detector module as claimed in claim 1, further comprising:

a number of power units, wherein the at least one subset of the plurality of heating subregions that is interconnected via the wiring unit is connected to a shared power unit for the supply of power.

3. The detector module as claimed in claim 1, wherein interconnection of the at least one subset of the plurality of heating subregions via the wiring unit includes a parallel connection of at least two of the plurality of heating subregions or a series connection of at least two of the plurality of heating subregions.

4. The detector module as claimed in claim 1, wherein the interconnection of the at least one subset of the plurality of heating subregions via the wiring unit includes a combination of a parallel connection and a series connection of heating subregions of the at least one subset of the plurality of heating subregions, such that when power is supplied to the at least one subset of the plurality of heating subregions, the interconnection sets a fixed ratio between power present in respective ones of the heating subregions in the at least one subset of the plurality of heating subregions.

5. The detector module as claimed in claim 2, wherein the power provided by a particular power unit for heating subregions connected thereto is based on at least one of an expected or a measured temperature in the stacked structure.

6. The detector module as claimed in claim 1, wherein at least one temperature sensor is in the stacked structure.

7. The detector module as claimed in claim 1, wherein the heating layer is applied to a face of the readout layer or integrated in the readout layer.

8. The detector module as claimed in claim 1, wherein the wiring unit is a printed circuit board.

9. The detector module as claimed in claim 1, wherein the sensor layer includes a direct converting semiconductor material.

10. The detector module as claimed in claim 2, wherein the stacked structure is on a module carrier, the module carrier being thermally coupled to the sensor layer via the stacked structure.

11. The detector module as claimed in claim 10, wherein the wiring unit is connected to a module electronic circuit via the module carrier.

12. The detector module as claimed in claim 11, wherein the module electronic circuit includes the number of power units.

13. The detector module as claimed in claim 10, wherein a number of stacked structures are adjacent to one another on the module carrier.

14. An X-ray detector configured to acquire images of an object, the X-ray detector comprising:

a plurality of adjacently arranged detector modules as claimed in claim 1.

15. A computed tomography device comprising:

the X-ray detector as claimed in claim 14; and an X-ray source opposite to the X-ray detector, wherein the X-ray source is configured to emit X-ray radiation onto the X-ray detector.

16. The detector module as claimed in claim 9, wherein the direct converting semiconductor material is cadmium telluride or cadmium zinc telluride.

17. The detector module as claimed in claim 1, wherein the stacked structure is on a module carrier, the module carrier being thermally coupled to the sensor layer via the stacked structure.

18. The detector module as claimed in claim 17, wherein the wiring unit is connected to a module electronic circuit via the module carrier.

19. The detector module as claimed in claim 2, wherein interconnection of the at least one subset of the plurality of heating subregions via the wiring unit includes a parallel connection of at least two of the plurality of heating subregions or a series connection of at least two of the plurality of heating subregions.

20. The detector module as claimed in claim 2, wherein the interconnection of the at least one subset of the plurality of heating subregions via the wiring unit includes a combination of a parallel connection and a series connection of heating subregions of the at least one subset of the plurality of heating subregions, such that, when power is supplied to the at least one subset of the plurality of heating subregions, the interconnection sets a fixed ratio between power present in respective ones of the heating subregions in the at least one subset of the plurality of heating subregions.

* * * * *